United States Patent [19]

Felger et al.

[11] Patent Number: 4,720,494

[45] Date of Patent: Jan. 19, 1988

[54] ANTICHOLINERGIC EUCATROPINE ESTERS AND ANTIPERSPIRANT USE THEREOF

[75] Inventors: Carl Felger, College Park, Md.; Edith Shulman, Grapevine, Tex.

[73] Assignee: The Gillette Company, Boston, Mass.

[21] Appl. No.: 668,049

[22] Filed: Nov. 5, 1984

[51] Int. Cl.$^4$ ............... A61K 31/495; A61K 31/445; C07D 401/12; C07D 211/46

[52] U.S. Cl. ..................... 514/252; 544/406; 546/170; 546/193; 546/222; 514/314; 514/318; 514/327

[58] Field of Search ............ 546/222, 193, 170; 514/327, 318, 314, 252; 544/406

[56] References Cited

U.S. PATENT DOCUMENTS

| | | | |
|---|---|---|---|
| 3,953,599 | 4/1976 | MacMillan et al. | 514/304 |
| 4,022,787 | 5/1977 | Soldati et al. | 546/222 |
| 4,226,999 | 10/1980 | Malherbe et al. | 546/222 |
| 4,517,176 | 5/1985 | Felger | 514/770 X |
| 4,546,096 | 10/1985 | Herlihy et al. | 536/18.2 X |

FOREIGN PATENT DOCUMENTS 58-159460  9/1983  Japan ................... 546/222

OTHER PUBLICATIONS

Morichi, Chem. Abstracts, vol. 54, 1960, entry 6971F.

Primary Examiner—Donald G. Daus
Assistant Examiner—William A. Teoli, Jr.
Attorney, Agent, or Firm—Mandel E. Slater

[57] ABSTRACT

This invention relates to novel chemical compounds, methods and compositions for inhibiting the production of human perspiration, especially axillary perspiration. More particularly, the practice of the invention comprises the topical application to the axiallary area or other perspiration-producing portion of the body of an anticholinergic eucatropine ester having reduced mydriatic activity and distributed in a suitable dermatologically acceptable carrier.

10 Claims, No Drawings

ANTICHOLINERGIC EUCATROPINE ESTERS AND ANTIPERSPIRANT USE THEREOF

BACKGROUND OF THE INVENTION

Metal salts having astringent properties are widely used to inhibit human axillary perspiration. While aluminum salts are most widely used, zinc salts have found some favor, and zirconium salts have recently become commercially important. Salts of many other metals have antiperspirant activity, but because of considerations of cost, availability, toxicity, color problems or the like, are not generally useful. Commonly used anions of the metal salts include the chloride or chloride and hydroxide, but other anions such as the sulfate, sulfamate, phenolsulfonate, bromide, iodide, nitrate, and lactate have been disclosed in the art as being useful.

One of the problems encountered in formulating antiperspirants based on acidic astringent metal salts is that fabrics with which they come into contact are often weakened. In addition, persons having sensitive or broken skin can experience irritation presumably caused by the low pH of such formulations. To overcome these problems, it is necessary to incorporate buffers such as urea and amino acids to adjust and control the pH. Sometimes basic metal salts can be employed to give a somewhat higher pH. In addition various active ingredients or additives intended to decrease fabric damage or increase mildness to the skin have been disclosed in the art. A further problem in the use of astringent metal salts is that the difficulty in preparing smooth, cosmetically acceptable formulations increases with increasing amounts of metal salt.

A further drawback in the use of astringent metal antiperspirants is the fact that considerable time can elapse between their application and the perception of their desired effect. The antiperspirant effect is not fully developed in most people for several hours, and maximum effectiveness is obtained only after regularly repeated usage over a period of days or weeks. Even more serious, a portion of the population is unable to achieve control of perspiration by the use of astringent metal salt antiperspirants. At best, such compositions, containing relatively large amounts of metallic salts, will provide about 40–50% reduction in perspiration in the axillae.

Anticholinergic agents have been used by the medical profession for the systemic and topical treatment of certain pathological cases of excessive sweating. They have also been suggested in the literature as possible ingredients of cosmetic antiperspirants.

In defining "anticholinergic," it is necessary to briefly describe certain aspects of human perspiration. Eccrine sweat glands, which secrete most of the liquid perspiration, are activated by a chemical mediator, usually considered to be acetylcholine, which is liberated at nerve endings when they are properly stimulated. An anticholinergic compound is one which destroys the action of the acetylcholine, probably by blocking the receptor sites of the secretory cells of the sweat glands, so that the cells are unable to respond. In addition to the eccrine glands, which are widely distributed over the surface of man's body, there are apocrine sweat glands which are fewer in number and are localized in particular areas including the axillae. Examples of anticholinergic compounds used in classical studies of perspiration inhibition include scopolamine and atropine.

In spite of the fact that such anticholinergics have been known to be useful in controlling human perspiration, satisfactory anticholinergic formulations for cosmetic and medical use have not been developed, the chief difficulty being to achieve adequate inhibition of perspiration at a level of usage which is physiologically safe.

A major problem in employing anticholinergic compounds heretofore for the control of human perspiration revolves about the mydriatic activity of such compounds on the eye. The risk of mydriasis has been especially great when anticholinergic compounds have been formulated as the active ingredient in antiperspirant products packaged in a manner presenting an increased risk of accidental instillation into the eye of the user. While it is possible to reduce the risk of mydriasis by reducing to a minimum the concentration of the active anticholinergic ingredient, it has generally been felt that the risks have outweighed the benefits.

BRIEF SUMMARY OF THE INVENTION

It has now been found that there exists a group of eucatropine ester derivatives having reduced mydriatic potency when compared with eucatropine and having a significant antiperspirancy potential as measured by the standard mouse foot antiperspirancy assay.

DETAILED DESCRIPTION OF THE INVENTION

It is known from the literature that the antisecretory activity of anticholinergics such as eucatropine is antimuscarinic. The literature also states that anticholinergics exhibiting a separation of antispasmodic and mydriatic properties are not known. However, during the course of our research, we have found that esters of eucatropine show reduced mydriasis when instilled in the eye yet still exhibit antiperspirant activity in animal models. Clearly, the possibility of separation of mydriatic and antisecretory properties has been demonstrated. In addition, studies indicate that the compounds are stable with little hydrolysis occurring even at elevated pH values indicating that the esters themselves are active antiperspirants.

The eucatropine esters used in the practice of our invention may be prepared by two distinct synthetic routes which lead to products having the same molecular structure but differing splits between antiperspirancy and mydriatic activity. A simple, effective method of esterification which utilizes free acids and dicyclohexylcarbodiimide (DCC) as reactants with 4-pyrrolidino-pyridine (4-PP) as a catalyst is our preferred method. Preparation of eucatropine esters via this method affords an easily isolatable compound in good yield.

As shown below, esters of various classes were prepared to determine if trends would become apparent that might point to a structure-activity relationship which would enable tailoring of molecules to provide maximal antiperspirant activity with concomitant minimal mydriatic activity. The classes chosen included flat, electron-rich moieties typified by aromatic rings; plus nitrogen heterocyclics, cycloaliphatics, and aliphatics.

PROCEDURE FOR SYNTHESIS OF ESTERS VIA DICYCLOHEXYLCARBODIIMIDE (DCC) REACTION

Eucatropine.HCl + RCOOH +

Dicyclohexylcarbodiimide (DCC) $\xrightarrow[\text{methylene chloride}]{\text{4-pyrrolidinopyridine}}$ Eucatropine ester.HCl + Dicyclohexylurea Into a round-bottom flask fitted with a magnetic stirrer and condenser capped with a calcium sulfate drying tube was charged 0.076 mol eucatropine.HCl, 0.12 mol acid of choice, 0.011 mold 4-pyrrolidinopyridine and 100 mL methylene chloride. To the stirred heterogeneous mixture was added 0.12 mol DCC in methylene chloride. Upon addition of the DCC, reactions were generally mildly exothermic causing gentle reflux. Reflux was maintained for 24 hours by heating the reaction flask in an oil bath maintained at 50°–55° C. After the reaction was complete, the mixture was cooled to room temperature then suction filtered through Celite to remove dicyclohexylurea. The methylene chloride was evaporated in vacuo and the residue, usually an amber oil, taken up in 300 mL distilled water. The pH was adjusted, if necessary, to 4.5–5.0 with 1.0M HCl. More solid, unreacted acid usually formed and the mixture was suction filtered through Celite to remove this material. The filtrate was extracted three times with 200 mL of ethyl ether and the ether layers discarded. The aqueous layer was adjusted to pH 8.5 with 1.0M NH4OH at which point the ester oiled out. The mixture was extracted three times with 150 mL of ethyl ether and the aqueous layer discarded. The combined ether layers were extracted three times with 150 mL of distilled water. The ether solution, containing the ester-free base, was gravity filtered through hydrophobic filter paper to remove water and finally evaporated in vacuo. The yellow-to-amber oil was dissolved in about 400 mL of 50% ethanol and pH adjusted to 4.5 to 5.0 with 1.0N HCl. The solution was rotary evaporated in vacuo. The product was generally redissolved in ethanol and the solvent re-evaporated several more times to remove as much water as possible.

The product was crystallized by dissolving in minimal hot chloroform or absolute alcohol, cooling to room temperature, then adding anhydrous ethyl ether just to the cloud point. The cloudy solution was warmed to remove some of the ether. When just clear, the solution was allowed to cool and then stand at room temperature for several hours. In some cases, nucleation occurred and the mixture was allowed to stand at room temperature until crystallization was complete. More commonly, the solution had to be refrigerated to effect crystallization. Typically, two subsequent recrystallizations were generally sufficient to yield pure compounds, as determined by TLC on silica gel plates and reverse phase HPLC on $C_{18}$ columns.

The synthesis of esters of eucatropine may also be accomplished through the use of acid chlorides. This reaction, however, leads to a number of by-products and yields are generally lower.

PROCEDURE FOR THE SYNTHESIS OF ESTERS VIA ACID CHLORIDES

Eucatropine.HCl + RCOCl $\xrightarrow{\text{pyridine}}$

Eucatropine ester.HCl + Pyridine.HCl

Into a round bottom flask equipped with a magnetic stirrer, pressure-equalizing addition funnel, and condenser capped with calcium sulfate drying tube (all glassware predried at 105° C.) were charged 0.0244 mol eucatropine.HCl and 25 mL pyridine (dried over BaO and filtered). The addition funnel was charged with 0.0517 mol of the acid chloride of choice. The acid chloride was added dropwise to the stirred reaction mixture over approximately a five-minute period. Reactions were exothermic and were generally allowed to proceed at self-regulating temperature. For extremely reactive acid chlorides, an ice-water bath was used for gentle cooling. Once the exotherm subsided, the reaction was allowed to proceed at self-regulating temperature for 18 to 24 hours. In cases where the mixture became too thick to stir, an additional 25 mL of pyridine was added without detriment.

At the end of the reaction period, the mixture was poured over approximately 20 grams of ice to quench unreacted acid chloride and the residue in the flask rinsed into the ice mixture with distilled water. To this was added 4.8 grams of sodium carbonate in 40 mL distilled water. Subsequently, sufficient solid anhydrous sodium carbonate was added, in small increments, to bring the pH to 8.5 to 9.0 (usually 3.5 to 4.0 grams). At this point a solid, which was difficult to filter, was sometimes present. The mixture was extracted three times with 100 mL of ethyl ether and the aqueous layer discarded. The combined ether layers were extracted three times with 100 mL of distilled water and the aqueous layers discarded. The ether solution was gravity-filtered through hydrophobic filter paper to remove water and evaporated in vacuo. The residue was taken up in approximately 100 mL of absolute ethanol. Any solid which formed at this point was filtered and discarded. Approximately 100 mL distilled water was added to the ethanol solution and the pH then adjusted to 4.5 to 5.0 with 1.0N HCl. Any solid which formed at this point was again filtered off and discarded. The remaining solution was evaporated to dryness in vacuo. The residue was redissolved in approximately 100 mL absolute ethanol and re-evaporated at least twice more to remove water and residual pyridine.

Crystallization and recrystallizations are effected as described for the DCC method.

MOUSE FOOT ANTIPERSPIRANT ASSAY

In order to determine the potential of the anticholinergic compounds used in the practice of our invention to inhibit sweating, antiperspirant activity was screened utilizing the mouse foot antiperspirant assay. This procedure, a simple, rapid and inexpensive screening study, is generally performed to generate a dose-response curve, the results of which can then be used to rank relative efficacy in a group of compounds.

For the dose-response determination, four or five groups of 10 ICR/CD-1 male albino mice weighing approximately 20 gm were used. The animals were anaesthetized with 0.20 mL of a 250 mg/mL solution of ethyl carbamate injected intraperitoneally. Anticholinergic test solutions using 0.9% aqueous sodium chloride were injected subcutaneously under the plantar foot pads of the right hind feet of 10 mice per concentration. The 26 gauge, 2 in. needle of a Hamilton 5 µL syringe was inserted at the rear of the plantar surface and threaded forward. The dose, 5 µL, was delivered subcutaneously near the interdigital foot pads. Subsequently, both hind feet were coated with a 1:1 suspension of soluble starch in 2% ethanolic iodine-castor oil.

At 5 minutes after test solution injection, sweating was stimulated by injecting each animal intraperitoneally with 0.20 mL of 1 mg/mL pilocarpine.HCl in 0.9% aqueous sodium chloride. The appearance of blue-black spots within five minutes after stimulation by pilocarpine was the criterion for sweating. The criterion for the animals responding to the anticholinergic was absence of sweating on two or more tubercles of the treated foot. A 7X magnifying glass was used to enlarge the foot for evaluation.

As many concentrations were tested as needed to obtain two points with more than 50% but less than 100% of the animals responding and two points with less than 50% but more than 0% of the animals responding.

Concentration intervals varied two-fold (log interval: 0.301) up or down from the initial concentration. For some esters it was necessary to alter the concentration interval to obtain the appropriate spread of responses in a minimum of trials. The median effective concentration ($EC_{50}$ with its 95% confidence limits) was estimated by the method of Litchfield and Wilcoxon. Each compound was run at least twice. The average $EC_{50}$ was used for comparison with other anticholinergics.

RABBIT ABOLITION OF LIGHT REFLEX ASSAY (RALR)

In order to determine the potential for mydriasis produced by the anticholinergic antiperspirant compositions of our invention, the rabbit abolition of light reflex assay was employed. In this assay, solutions of test compounds are instilled in the eyes of rabbits and response to light stimulus followed as a function of time.

The test animals used were female, New Zealand albino rabbits which were 12 to 14 weeks old when first used for testing. A test group consisted of fifteen animals and could be used 8 to 10 weeks before the rabbits became too large to handle.

Prior to the first use of a rabbit group, a determination of the responsiveness of each pupil to a light stimulus was determined. Under room illumination provided by fluorescent tubes, the bilateral symmetry of the pupil light reflex was ascertained by directing a beam of light from a penlight-type of flashlight into each pupil. If proper response was present, the animals were subsequently used.

The mydriatic response to an anticholinergic was determined in the following manner. The animals were held in wooden restrainer boxes during the test. The distance between the mid-sagittal plane of one animal and that of the immediately adjacent animal was 11 inches. Into one conjunctival sac of each animal was installed 0.1 mL of a given concentration of the compound under test in 0.9% sodium chloride. The concentration used was based on the level of parent compound that initiated an incomplete response in eight out of eight rabbits at 60 minutes. Thus, for eucatropine derivatives, solutions were prepared to correspond to one percent eucatropine.HCl. After installation of the solution, the lids of the treated eye were held closed for one minute to prevent the loss of the test dose. After this time the lids were held open by gentle finger pressure, and the cornea and conjunctival sac irrigated with one mL of 0.9% aqueous sodium chloride applied in drops from a 10 mL syringe. The procedure was repeated in the other eye using 0.1 mL 0.9% saline as a control. Each rabbit was treated at two to three minutes following the preceding rabbit.

Observation of the rabbit eye pupil size was made at 30, 60 and 120 minutes after treatment by directing a penlight beam into each pupil. The response of both pupils to light was observed. Any degree of contraction of the pupil of the treated eye which was obviously less than that of the untreated eye was recorded as incomplete (partial) inhibition of the reflex. Failure of the pupil of the treated eye to contract in response to light was recorded as complete inhibition of the reflex. The responses of each rabbit were recorded. Both partial and complete inhibition were recorded as inhibited. The animals were not used again for at least 72 hours and the same eye was not used for treatment by test solutions in successive experiments.

The eye response of the rabbit group at 60 minutes was used for comparison of mydriatic activity among any group of compounds and results expressed as the fraction of animals exhibiting inhibition relative to the total test population.

EXAMPLE I

Evaluation of Aromatic Esters of Eucatropine

Among the aromatic esters, various substituted benzenoid structures were investigated (Table I) to determine if electron distribution properties in the aromatic nucleus had an effect on $EC_{50}$ and mydriasis. The toluate, p-methoxybenzoate, and 4-dimethylaminobenzoate all contained electron-donating groups (making the aromatic nucleus more electron-rich) while the p-chlorobenzoate and p-nitrobenzoate were representative of electron-deficient aromatic nuclei. As the data in Table I indicate, no trends emerged that would indicate that the electronic characteristics of the aromatic nucleus of benzoate analogs could be manipulated to increase antiperspirancy. Interestingly, however, moving the aromatic nucleus one carbon away from the ester linkage (phenylacetate) or introducing a more labile ester group (α-chlorophenylacetate) afforded compounds whose potency equalled or nearly equalled that of the parent eucatropine. It should also be noted that the benzoate prepared by the DCC method yielded an ester which was more potent than eucatropine.

When these esters were biologically tested for mydriatic effects, most were found to exhibit reduced mydriasis.

TABLE I

AROMATIC EUCATROPINE ESTERS

| Ester Group | Synthesis Method | $EC_{50}$ (M) | RALR[a] (60 min.) |
|---|---|---|---|
| H | — | $7.2 \times 10^{-3}$ | 1.00 |
| Benzoate | DCC | $3.0 \times 10^{-4}$ | 0.87 |
| p-Toluate | DCC | $8.4 \times 10^{-2}$ | 0.40 |
| p-Methoxybenzoate | DCC | $1.6 \times 10^{-2}$ | 0.47 |
| p-Chlorobenzoate | DCC | $5.3 \times 10^{-2}$ | 0.73 |
| p-Nitrobenzoate | DCC | $1.2 \times 10^{-1}$ | 0.67 |
| 4-Dimethylaminobenzoate | DCC | $2.5 \times 10^{-2}$ | 0.27 |
| Phenylacetate | DCC | $5.3 \times 10^{-3}$ | 1.00 |

TABLE I-continued

| AROMATIC EUCATROPINE ESTERS | | | |
|---|---|---|---|
| Ester Group | Synthesis Method | $EC_{50}$ (M) | $RALR^a$ (60 min.) |
| α-Chlorophenylacetate | DCC | $1.4 \times 10^{-3}$ | 0.87 |

[a]1% solutions based on eucatropine

EXAMPLE II

Evaluation of Nitrogen Heterocyclic Esters of Eucatropine

In order to determine if the presence of a second nitrogen atom in the eucatropine ester molecule would affect properties, several nitrogen heterocyclic systems were synthesized (Table II). In the isonicotinate-nicotinate-picolinate series, where the pyridine ring nitrogen is para, meta, or ortho, respectively, to the ester linkage, only a slight decrease in antiperspirant potency relative to eucatropine was found. In addition, the isonicotinate effected no mydriasis in the rabbit eye.

Further investigation of this class of esters was warranted. Thus 2-pyrazinecarboxylate, a dinitrogen analog of pyridine, and 3- and 4-quinoline carboxylates in which an additional aromatic nucleus is incorporated into the nitrogen moiety, were synthesized. Biological evaluations showed a reduction in $EC_{50}$ over eucatropine as well as reduced mydriasis.

TABLE II

| NITROGEN HETEROCYCLIC EUCATROPINE ESTERS | | | |
|---|---|---|---|
| Ester Group | Synthesis Method | $EC_{50}$ (M) | $RALR^a$ (60 min.) |
| Isonicotinate | DCC | $5.2 \times 10^{-3}$ | 0.00 |
| Nicotinate | DCC | $6.5 \times 10^{-3}$ | 0.60 |
| Picolinate | DCC | $2.0 \times 10^{-3}$ | 0.40 |
| 2-Pyrazinecarboxylate | DCC | $1.1 \times 10^{-2}$ | 0.80 |
| 3-Quinolinecarboxylate | DCC | $1.0 \times 10^{-2}$ | 0.73 |
| 4-Quinolinecarboxylate | DCC | $1.4 \times 10^{-1}$ | 0.60 |

[a]1% solutions based on eucatropine

EXAMPLE III

Evaluation of Cycloaliphatic and Aliphatic Esters of Eucatropine

To evaluate the effects of electron poor and/or bulky ester moieties, a series of cycloaliphatic and aliphatic esters were synthesized and evaluated with the results as shown (Tables III and III-A).

TABLE III

| Ester Group | Synthesis Method | $EC_{50}$ (M) | $RALR^a$ (60 min.) |
|---|---|---|---|
| CYCLOALIPHATIC EUCATROPINE ESTERS | | | |
| Cyclopropanecarboxylate | DCC | $4.7 \times 10^{-3}$ | 1.00 |
| Cyclobutanecarboxylate | DCC | $1.8 \times 10^{-2}$ | 1.00 |
| Cyclopentanecarboxylate | DCC | $7.8 \times 10^{-2}$ | 0.67 |
| Cyclohexanecarboxylate | DCC | $4.1 \times 10^{-2}$ | 1.00 |
| Cyclopentylacetate | DCC | $6.7 \times 10^{-2}$ | 1.00 |
| Cyclohexylacetate | DCC | $8.7 \times 10^{-2}$ | 0.67 |
| ALIPHATIC EUCATROPINE ESTERS | | | |
| Isobutyrate | DCC | $1.6 \times 10^{-3}$ | 0.88 |
| Octanoate | DCC | $1.1 \times 10^{-2}$ | 0.93 |

[a]1% solutions based on eucatropine

EXAMPLE IV

Effect of Synthesis Method on Biological Properties of Eucatropine Esters

As mentioned hereinabove, the eucatropine esters used in the practice of our invention may be prepared by two distinct synthetic routes which lead to products having the same molecular structure but differing splits between antiperspirancy and mydriatic activity. To illustrate that the synthesis route does indeed play a role in the mydriatic properties of esters, several esters synthesized via the DCC route were resynthesized via acid chlorides. The esters chosen were aromatic, cycloaliphatic, and aliphatic and were representative of those obtained via DCC. Data from the biological evaluations of these acid chloride-derived esters are presented in Table IV. Indeed, these esters exhibited differences in mydriasis after installation in the rabbit eye over those prepared via the DCC method. Also, except for the cyclohexanecarboxylate and the octanoate, the $EC_{50}$ of esters derived via acid chlorides were lower than those derived via DCC.

TABLE IV

| EFFECTS OF SYNTHESIS METHOD ON BIOLOGICAL PROPERTIES OF EUCATROPINE ESTERS | | | |
|---|---|---|---|
| Ester Group | Synthesis Method | $EC_{50}$ (M) | $RALR^a$ (60 min.) |
| Benzoate | DCC | $3.0 \times 10^{-4}$ | 0.88 |
| | Acid Chloride | $2.5 \times 10^{-2}$ | 0.20 |
| Cyclohexanecarboxylate | DCC | $4.1 \times 10^{-2}$ | 1.00 |
| | Acid Chloride | $4.3 \times 10^{-2}$ | 0.13 |
| Cyclopropanecarboxylate | DCC | $4.8 \times 10^{-3}$ | 1.00 |
| | Acid Chloride | $3.6 \times 10^{-2}$ | 1.00 |
| Phenylacetate | DCC | $5.3 \times 10^{-3}$ | 1.00 |
| | Acid Chloride | $7.8 \times 10^{-2}$ | 0.47 |
| Octanoate | DCC | $1.1 \times 10^{-2}$ | 0.93 |
| | Acid Chloride | $9.6 \times 10^{-3}$ | 0.50 |
| p-Toluate | DCC | $8.4 \times 10^{-2}$ | 0.40 |
| | Acid Chloride | $4.3 \times 10^{-1}$ | 0.80 |
| p-Methoxybenzoate | DCC | $1.6 \times 10^{-2}$ | 0.47 |
| | Acid Chloride | $1.1 \times 10^{-1}$ | 0.67 |
| p-Chlorobenzoate | DCC | $5.3 \times 10^{-2}$ | 0.73 |
| | Acid Chloride | $2.5 \times ^{-1}$ | 0.27 |
| α-Chlorophenylacetate | DCC | $1.4 \times 10^{-3}$ | 0.87 |
| | Acid Chloride | — | 0.00 |

[a]1% solutions based on eucatropine

FORMULATIONS FOR ANTIPERSPIRANT USE

The concentration of anticholinergic eucatropine ester employed in topical compositions for application to the human body should be consistent with the requirements of efficacy, safety and economy. These requirements can often be met with extremely small amounts of active ingredient, e.g., a small but perceptible amount of as little as about 0.01% by weight. We prefer to employ from about 0.01 to about 2% by weight. As indicated above, the present compositions may include the principal active ingredient either alone or in combination with other active materials. Accordingly, other antiperspirants such as the aluminum salts, zinc salts and zirconium salts (e.g., the chlorides, chlorhydroxides and sulfates) in concentrations of from about 5 to about 25 percent may be employed as supplementary active ingredients. Additionally, combinations of the principal active ingredients with antibacterial agents suitable for topical deodorant use offer a balanced approach to the problem. Such combinations include substances capable of minimizing bacterial action on available organic secretions in the affected areas, thereby supplementing the primary activity. The various known antibacterials with demonstrated effectiveness in this function are appropriate for use in the present compositions.

Dermatologically acceptable carriers into which the active ingredients may be incorporated to produce satisfactory antiperspirant compositions include those commonly employed for topical application of cosmetics or pharmaceuticals. Such carriers or vehicles include lotions, ointments, aerosols, water solutions, creams (preferably of the oil-in-water type), pulverulent mixtures, gelled sticks and the like. Depending on the physical nature of the vehicle or carrier employed, the method of this invention can be practiced by applying such compositions topically from a roll-on applicator, by a brush or pad, by sprinkling on the skin, from a squeeze bottle, by spraying under propellant pressure, and in other manners according to the particular type of carrier employed.

The compositions of this invention should be formulated to have a pH in aqueous solution of not less than about 3.0 nor more than about 6.5 since hydrolytic stability is greatest at lower pH's. It should be noted that irritation of the skin may be encountered at pH's lower than 3. At pH's above about 6.5 and especially at elevated temperatures, hydrolysis of the eucatropine ester can occur at a rate such that a significant change of antiperspirant or mydriatic activity may occur.

In preparing the desired product form of the present compositions, various additives, diluents and adjuvants can be utilized. These illustratively include perfumes, essential oils, surfactants (e.g., polysorbate 80, polyoxyethylene sorbitan trioleate, sodium lauryl sulfate, sodium cetyl sulfate), emulsifiers, (e.g., glyceryl monostearate-diethylaminoethyl alkyl amide phosphate, isopropyl myristate, cetyl alcohol, glyceryl and glycol esters of stearic acid), alcohols (e.g., ethanol and isopropanol), glycols (e.g., propylene glycol, glycerol, sorbitol), ointment-type bases (e.g., spermaceti, carbowaxes, beeswax), higher fatty acids (e.g., stearic acid, palmitic acid), propellants (e.g., halogenated hydrocarbons, carbon dioxide, nitrogen), silicone-type fluids (e.g., polysiloxane fluid), and solid diluents (e.g., calcium carbonate, starch, bentonite, talc).

The following composition examples disclose formulations with the eucatropine esters denoted as "active antiperspirant compound."

EXAMPLE V

Cream Antiperspirant Composition

A cream antiperspirant composition is prepared by mixing together the ingredients of the following recipe in which the parts are by weight.

| Ingredient | Parts |
| --- | --- |
| Condensate of ethylene oxide with a hydrophobic base formed by condensing propylene oxide with propylene glycol (Pluronic F-68) | 5.0 |
| Active antiperspirant compound | 1.0 |
| Cetyl trimethyl ammonium bromide | 0.5 |
| Cetyl alcohol | 1.0 |
| Glyceryl monostearate | 13.0 |
| Spermaceti wax | 4.0 |
| Glycerine | 3.0 |
| Polyoxyalkylene propylene glycol monostearate | 0.5 |
| Polyoxyalkylene stearate | 0.5 |
| Ethanol | 10.0 |
| Perfume | 0.1 |
| Water, q.s. | 100 |

The foregoing composition when used daily is effective in reducing axillary perspiration. Repeated applications have less tendency to cause irritation to the skin than do similar compositions containing conventional astringent antiperspirants, similarly causing less irritation when applied to freshly shaved areas of the skin.

EXAMPLE VI

Lotion Antiperspirant Composition

The following lotion composition is prepared in which the parts are by weight:

| Ingredient | Parts |
| --- | --- |
| Condensate of ethylene oxide with a hydrophobic base formed by condensing propylene oxide with propylene glycol (Pluronic F-68) | 10.0 |
| Active antiperspirant compound | 2.0 |
| 8-Hydroxyquinoline sulfate | 0.8 |
| Ethanol | 5.0 |
| Veegum | 3.5 |
| Mineral oil | 6.0 |
| Stearyl alcohol | 1.5 |
| Polyoxyalkylene propylene glycol monostearate | 0.8 |
| Polyoxyalkylene stearate | 0.8 |
| Perfume | 0.1 |
| Water, q.s. | 100 |

The composition, when applied to the skin, produces results similar to those obtained with the composition of Example V.

EXAMPLE VII

Liquid Antiperspirant Composition

The following liquid antiperspirant composition is prepared in which the parts are by weight.

| Ingredient | Parts |
| --- | --- |
| Condensate of ethylene oxide with a hydrophobic base formed by condensing propylene oxide with propylene glycol (Pluronic F-68) | 10.0 |
| Active antiperspirant compound | 0.05 |
| Aluminum chlorhydrol | 10.00 |
| Glycerine | 5.00 |
| Ethanol | 32.00 |
| Benzyl-dimethyl-alkyl ammonium chloride containing 8 to 18 carbon atoms in the alkyl group | 0.1 |
| Perfume | 0.2 |
| Water, q.s. | 100 |

When the composition is applied to the skin, the results obtained are similar to those obtained with the composition of Example V.

EXAMPLE VIII

Antiperspirant Stick Deodorant

An antiperspirant (and deodorant) in stick form is prepared by mixing together the following ingredients at elevated temperature, then pouring the composition into a mold and allowing it to solidify. The quantity of each ingredient in parts by weight is given below:

| Ingredient | Parts |
| --- | --- |
| Condensate of ethylene oxide with a hydrophobic base formed by condensing propylene oxide with propylene glycol (Pluronic F-68) | 2.0 |
| Active antiperspirant compound | 0.5 |
| Sodium stearate | 8.5 |
| Propylene glycol | 5.0 |
| Cetyl trimethyl ammonium bromide | 0.5 |
| Perfume | 0.1 |
| Ethyl alcohol, q.s. | 100 |

When rubbed on the skin, the stick provides similar results as are obtained with the composition of Example V.

EXAMPLE IX

Aerosol Antiperspirant

| Ingredient | Parts |
| --- | --- |
| Aluminum chlorhydrol | 11.9 |
| Active antiperspirant compound | 2.0 |
| Isopropyl myristate | 2.0 |
| Volatile silicone | 11.0 |
| Bentone | 1.0 |
| Ethyl alcohol | 2.0 |
| Perfume | 0.1 |

The above composition is packaged in a pressure container in the conventional manner along with 78 parts of a conventional liquified gaseous propellant.

When the liquid is sprayed upon the skin in the usual manner upon release from the pressurized package, it is found to be effective as an antiperspirant in the same manner as the compositions of the preceding examples.

While particular embodiments of the invention have been described, it will be apparent to those skilled in the art that variations may be made thereto without departing from the spirit of the invention and the scope of the appended claims.

We claim:

1. An ester of eucatropine having reduced mydriatic potency when compared with eucatropine and having a significant antiperspirancy potential as measured by the standard mouse foot antiperspirance assay, in which the ester group is benzoate, p-toluate, p-methoxybenzoate, p-chlorobenzoate, p-nitrobenzoate, 4-dimethylaminobenzoate, α-chlorophenylacetate, isonicotinate, nicotinate, picolinate, 2-pyrazinecarboxylate, 3-quinolinecarboxylate, 4-quinolinecarboxylate, cyclopentanecarboxylate, cyclohexanecarboxylate, cyclohexylacetate, isobutyrate, or octanoate.

2. An ester of eucatropine as described in claims 1 which has been prepared by reacting a eucatropine salt with a free acid and dicyclohexylcarbodiimide.

3. An ester of eucatropine as described in claims 1 which has been prepared by reacting a eucatropine salt with an acid chloride.

4. An antiperspirant composition comprising at least 0.01% by weight of an ester of eucatropine distributed in a dermatologically acceptable carrier in which the ester group is benzoate, p-toluate, p-methoxybenzoate, p-chlorobenzoate, p-nitrobenzoate, 4-dimethylaminobenzoate, α-chlorophenylacetate, isonicotinate, nicotinate, picolinate, 2-pyrazinecarboxylate, 3-quinolinecarboxylate, 4-quinolinecarboxylate, cyclopentanecarboxylate, cyclohexanecarboxylate, cyclohexylacetate, isobutyrate, and octanoate.

5. An antiperspirant composition as described in claim 4 and having a pH of about 3.0 to about 6.5.

6. An antiperspirant composition as described in claim 4 and containing an antiperspirant ingredient in addition to said ester of eucatropine.

7. An antiperspirant composition as described in claim 4 and containing an antibacterial agent suitable for topical deodorant use.

8. An antiperspirant composition as described in claims 4, 5, 6, or 7 in which said ester of eucatropine has been prepared by reacting a eucatropine salt with a free acid and dicyclohexylcarbodiimide.

9. An antiperspirant composition as described in claims 4, 5, 6, or 7 in which said ester of eucatropine has been prepared by reacting a eucatropine salt with an acid chloride.

10. The process of inhibiting perspiration which comprises the step of applying to the human body a composition comprising at least 0.01% by weight of an ester of eucatropine distributed in a dermatologically acceptable carrier in which the ester group is benzoate, p-toluate, p-methoxybenzoate, p-chlorobenzoate, p-nitrobenzoate, 4-dimethylaminobenzoate, α-chlorophenylacetate, isonicotinate, nicotinate, picolinate, 2-pyrazinecarboxylate, 3-quinolinecarboxylate, 4-quinolinecarboxylate, cyclopentanecarboxylate, cyclohexanecarboxylate, cyclohexylacetate, isobutyrate, and octanoate.

* * * * *